(12) United States Patent
Boerner et al.

(10) Patent No.: US 7,589,215 B2
(45) Date of Patent: Sep. 15, 2009

(54) BISPHOSPHINES AS BIDENTATE LIGANDS

(75) Inventors: Armin Boerner, Rostock (DE); Jens Holz, Kessin (DE); Axel Monsees, Frankfurt (DE); Thomas Riermeier, Floersheim (DE); Renat Kadyrov, Frankfurt (DE); Carsten A. Schneider, Frankfurt (DE); Uwe Dingerdissen, Seeheim-Jugenheim (DE); Karlheinz Drauz, Freigericht (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 11/609,559

(22) Filed: Dec. 12, 2006

(65) Prior Publication Data

US 2007/0179301 A1  Aug. 2, 2007

Related U.S. Application Data

(63) Continuation of application No. 10/508,537, filed as application No. PCT/EP03/02162 on Mar. 3, 2003, now abandoned.

(30) Foreign Application Priority Data

Apr. 4, 2002 (DE) .............................. 102 14 988

(51) Int. Cl.
C07F 9/572 (2006.01)
C07F 9/547 (2006.01)
(52) U.S. Cl. ...................................... 548/412; 549/216
(58) Field of Classification Search ................. 548/412; 549/216
See application file for complete search history.

(56) References Cited

U.S. PATENT DOCUMENTS

| 5,171,892 | A | 12/1992 | Burk |
| 6,476,246 | B2 | 11/2002 | Monsees et al. |
| 6,492,544 | B2 | 12/2002 | Krimmer et al. |
| 6,573,389 | B1 | 6/2003 | Bosch et al. |
| 2005/0209455 | A1 | 9/2005 | Boerner et al. |
| 2007/0149781 | A1 | 6/2007 | Riermeier et al. |
| 2007/0179301 | A1 | 8/2007 | Boerner et al. |

FOREIGN PATENT DOCUMENTS

WO   03/031456   4/2003

OTHER PUBLICATIONS

Holz et al. "Synthesis of a New Chiral Bisphospholane Ligand for the Rh(I)-Catalyzed Enantioselective Hydrogenation of isomeric beta-Acylamido Acrylates" Journal of Organic Chemistry, 2003, vol. 68, pp. 1701-1707.*
Fenske et al. "2,3-Bis(diphenylphosphino)maleinsaureanhydrid und Dipehneyl-phosphinoderivate des Cyclobutendions als Liganden in Metallcarbonylen" Chem. Berichte, 1974, vol. 107, pp. 117-122.*

Kinting, Annegret et al. "Asymmetric Hydrogenation Catalyzed by Rhodium Complexes of 2,3-Bis(Dimenthylphosphino)Maleic Anhydride and 2,3-Bis(Dimethylphosphino)-N-Phenylmaleimide", Journal of Organometallic Chemistry, vol. 302, No. 2, pp. 259-264, XP002244123 1986.
Becher, Hermann J. et al. "Diphenylphosphinoderivate von Malein- und Fumarsaeureestern: Darstellung, Elgenschaften; Kristall- und Molekuelstrukturen", Monatshefte fuer Chemie, vol. 109, No. 5, pp. 1023-1036, XP002244124, with English abstract 1978.
Berglund, Mats et al. "Chelating Phosphines on Silica Gel. I. Carbonyl Complexes as a Mean to Probe Chelating Ligand Sites", Journal of Organometallic Chemistry, vol. 258, No. 2, pp. 195-204, XP002244125 1983.
Avey, Alfred et al. "A New Water-Soluble Phosphine for Use in Aqueous Organometallic Systems. Products from the Reactions of 2,3-Bis(diphenylphosphino)maleic Anhydride with Water and Oxygen", Inorg. Chem., vol. 32, No. 2, pp. 233-236, XP001157596 1993.
Fenske, Dieter et al. "Darstellung und Eigenschaften von Derivaten des 2,3-Bis(diphenylphosphino)maleinsaeure-anhydrids als Beitrag zum Problem der Farbigkeit, Konjugationsbeeinflussung und Komplexbildung dieser Stoffklasse", Chem. Ber., vol. 108, No. 6, pp. 2115-2123, XP002244186, with English abstract 1975.
Fenske, Dieter et al. "2,3-Bis(diphenylphosphino)maleinsaeureanhybrid und Diphenyl-phosphinoderivate des Cyclobutendions als Liganden In Metallcarbonylen", Chem. Ber., vol. 107, No. 1, pp. 117-122, XP002244187, with English abstract 1974.
Holz, Jens et al. "Synthesis of a New Chiral Bisphospholane Ligand for the Rh(I)-Catalyzed Enantioselective Hydrogenation of Isomeric beta-Acylamido Acrylates", J. Org. Chem. vol. 68, No. 5, pp. 1701-1707, XP002244188 2003.
Becher et al. "Radikalanionen des Bis (diphenylphosphino) maleinsaureanhydrid und seiner derivate Polarographische und ESR-Messungen Praparative Anwendungen" Zeitschrift fur anorganisch und allgemeine chemie 1981, vol. 475, pp. 27-34.
U.S. Appl. No. 11/609,559, filed Dec. 12, 2006, Boerner, et al.
U.S. Appl. No. 11/609,606, filed Dec. 12, 2006, Boerner, et al.
U.S. Appl. No. 11/573,275, filed Feb. 6, 2007, Holz, et al.
U.S. Appl. No. 11/908,343, filed Sep. 11, 2007, Holz, et al.

* cited by examiner

*Primary Examiner*—Rei-Tsang Shiao
*Assistant Examiner*—Joseph R Kosack
(74) *Attorney, Agent, or Firm*—Oblon, Spivak, McClelland, Maier & Neustadt, P.C.

(57) ABSTRACT

The present invention relates to ligands of the general formula (I).

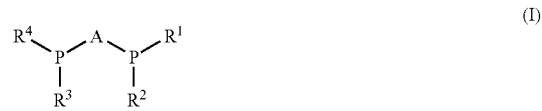

In addition, a process for the production thereof and the use thereof are demonstrated.

66 Claims, 1 Drawing Sheet

BISPHOSPHINES AS BIDENTATE LIGANDS

The present invention relates to bisphosphines as bidentate ligands, a process for the production thereof and their use. In particular, the invention concerns bisphosphines of the general structure (I).

(I)

Enantiomer-enriched chiral ligands are used in asymmetric synthesis or asymmetric catalysis. It is essential here for the electronic and stereochemical properties of the ligand to be optimally adapted to the particular catalysis problem. An important aspect of the success of these families of compounds is attributed to the creation of a particularly asymmetric environment of the metal centre by these ligand systems. To utilise such an environment for an effective transfer of chirality, it is advantageous to control the flexibility of the ligand system as an inherent limitation of the asymmetric induction.

Within the family of phosphorus-containing ligands, cyclic phosphines, particularly the phospholanes, have achieved particular significance. Bidentate, chiral phospholanes are, for example, the DuPhos and BPE ligands used in asymmetric catalysis. Ideally, therefore, a chiral ligand basic skeleton capable of versatile modification is available, which can be varied within broad limits in respect of its steric and electronic properties.

The object of this invention is therefore to provide a ligand skeleton analogous to that of the existing phospholane ligands, but which can additionally be varied and used within broad limits and possesses comparably good catalytic properties. In particular, the invention is based on the object of providing novel, asymmetric, bidentate and chiral phosphine ligand systems for catalytic purposes, which can be produced simply and with high enantiomeric purity.

These and other problems not otherwise specified but arising from the prior art are solved by a family of chiral bidentate bisphosphine compounds of the general formula (I), the compounds according to the invention having two chiral phosphine radicals bonded together via an unsaturated bridge.

By preparing enantiomer-enriched bidentate organophosphorus ligands of the general formula (I), (I)

wherein $R^1$, $R^2$, $R^3$, $R^4$, independently of one another, denote ($C_1$-$C_8$)-alkyl, ($C_2$-$C_8$)-alkoxyalkyl, ($C_6$-$C_{18}$)-aryl, ($C_7$-$C_{19}$)-aralkyl, ($C_3$-$C_{18}$)-heteroaryl, ($C_4$-$C_{19}$)-heteroaralkyl, ($C_1$-$C_8$)-alkyl-($C_6$-$C_{18}$)-aryl, ($C_1$-$C_8$)-alkyl-($C_3$-$C_{18}$)-heteroaryl, ($C_3$-$C_8$)-cycloalkyl, ($C_1$-$C_8$)-alkyl-($C_3$-$C_8$)-cycloalkyl, ($C_3$-$C_8$)-cycloalkyl-($C_1$-$C_8$)-alkyl, or $R^1$ and $R^2$ and/or $R^3$ and $R^4$ represent a ($C_3$-$C_5$)-alkylene bridge mono-or polysubstituted with ($C_1$-$C_8$)-alkyl, HO—($C_1$-$C_8$)-alkyl, ($C_1$-$C_8$)-alkoxy, ($C_2$-$C_8$)-alkoxyalkyl, ($C_6$-$C_{18}$)-aryl, ($C_7$-$C_{19}$)-aralkyl, ($C_1$-$C_8$)-alkyl-($C_6$-$C_{18}$)-aryl, ($C_3$-$C_8$)-cycloalkyl, ($C_1$-$C_8$)-alkyl-($C_3$-$C_8$)-cycloalkyl, ($C_3$-$C_8$)-cycloalkyl-($C_1$-$C_8$)-alkyl, this optionally being linked to a polymer enlargement, and A denotes one of the following structures wherein R denotes H, ($C_1$-$C_8$)-alkyl, ($C_6$-$C_{18}$)-aryl, ($C_7$-$C_{19}$)-aralkyl, ($C_1$-$C_8$)-alkyl-($C_6$-$C_{18}$)-aryl, ($C_3$-$C_8$)-cycloalkyl, ($C_1$-$C_8$)-alkyl-($C_3$-$C_8$)-cycloalkyl, ($C_3$-$C_8$)-cycloalkyl-($C_1$-$C_8$)-alkyl, or the link to a polymer enlargement, Q=O, NH, NR, previously unknown compounds are obtained, which can be successfully used in asymmetric catalysis for the production of organic compounds. Thus, with the ligands provided by the invention, complexes or catalysts can be produced for the successful hydrogenation of mixtures of acylated E- and Z-β-aminoacrylic acids or derivatives thereof, among other things. To date, only a few complexes have been successfully tested for mixtures of this family of compounds, and so up to now it has been necessary to perform an often complicated purification of the E/Z mixtures before hydrogenation, so as to be able to react the acylated E-β-aminoacrylic acids and derivates, which can only be hydrogenated with high enantiomeric excesses, separately from Z-components.

The ligands according to the invention preferably correspond to structures of the general formula (II), (II)

wherein

A takes on the meaning given above, $R^5$ to $R^{12}$, independently of one another, denote ($C_1$-$C_8$)-alkyl, HO—($C_1$-$C_8$)-alkyl, ($C_1$-$C_8$)-alkoxy, ($C_2$-$C_8$)-alkoxyalkyl, ($C_6$-$C_{18}$)-aryl, ($C_7$-$C_{19}$)-aralkyl, ($C_1$-$C_8$)-alkyl-($C_6$-$C_{18}$)-aryl, ($C_3$-$C_8$)-cycloalkyl, ($C_1$-$C_8$)-alkyl-($C_3$-$C_8$)-cycloalkyl, ($C_3$-$C_8$)-cycloalkyl-($C_1$-$C_8$)-alkyl, or the link to a polymer enlargement.

The ligand systems according to the invention can therefore be attached to a polymer enlargement. The ligands or the complexes/catalysts that can be produced from them can thus be separated very readily from the low molecular-weight compounds, e.g. by filtration, owing to the link to the polymer enlargement, and are thus accessible to the recycling desired by the invention, which is extremely simple but nonetheless advantageous. The ligands/complexes can be enlarged in molecular weight by linking to a polymer enlargement, and optionally heterogenised in this way. The enantioselective hydrogenation with complexes or catalysts that have been thus enlarged in molecular weight can therefore proceed in both a homogeneous and a heterogeneous phase.

Polymer Enlargement:

The polymer enlargement can be freely selected within the framework of the invention. It is limited on the one hand by considerations of practicability and costs, and on the other hand by prevailing technical conditions (retention capacity, solubility etc.). Some polymer enlargements for catalysts are known from the prior art (Reetz et al., Angew. Chem. 1997, 109, 1559f.; Seebach et al., Helv. Chim Acta 1996, 79, 1710f.; Kragl et al., Angew. Chem. 1996, 108, 684f.; Schurig et al., Chem. Ber./Recueil 1997, 130, 879f.; Bolm et al., Angew. Chem. 1997, 109, 773f.; Bolm et al. Eur. J. Org. Chem. 1998, 21f.; Baystone et al. in Speciality Chemicals 224f.; Salvadori et. al., Tetrahedron: Asymmetry 1998, 9, 1479; Wandrey et al., Tetrahedron: Asymmetry 1997, 8, 1529f.; ibid. 1997, 8, 1975f.; Togni et al. J. Am. Chem. Soc. 1998, 120, 10274f., Salvadori et al., Tetrahedron Lett. 1996, 37, 3375f; WO 98/22415; particularly DE 19910691.6; Janda et al., J. Am. Chem. Soc. 1998, 120, 9481f.; Andersson et al., Chem. Commun. 1996, 1135f.; Janda et al., Soluble Polymers 1999, 1, 1; Janda et al., Chem. Rev. 1997, 97, 489; Geckler et al., Adv. Polym. Sci. 1995, 121, 31; White et al., in "The Chemistry of Organic Silicon Compounds" Wiley, Chichester, 1989, 1289; Schuberth et al., Macromol. Rapid Commun. 1998, 19, 309; Sharma et al., Synthesis 1997, 1217; "Functional Polymers" Ed.: R. Arshady, ASC, Washington, 1996; "Praktikum der Makromolekularen Stoffe", D. Braun et al., VCH-Wiley, Weinheim 1999).

It is also preferred for the polymer enlargement to be formed by polyacrylates, polyacrylamides, polyvinylpyrrolidinones, polysiloxanes, polybutadienes, polyisoprenes, polyalkanes, polystyrenes, polyoxazolines or polyethers, or mixtures thereof. In an especially preferred embodiment, polystyrenes are used to construct the polymer enlargement.

Linkers:

Between the actual ligand and the polymer enlargement, a linker can be incorporated. The linker serves to create a distance between ligand and polymer to reduce or eliminate mutual interactions that are disadvantageous to the reaction.

The linkers can, in principle, be freely selected by the person skilled in the art. They should be selected according to the aspects of how well they can be coupled to the polymer/monomer on the one hand and to the ligand on the other hand. Suitable linkers can be found e.g. in the literature references mentioned above under the heading of "Polymer enlargement".

Within the framework of the invention, these active units of formulae (I) to (IV) are therefore advantageously bound to the polymer enlargement directly, or preferably via a linker selected from the group

| a) | —Si(R$_2$)— | |
| b) | —(SiR$_2$—O)$_n$— | n = 1-10000 |
| c) | —(CHR—CHR—O)$_n$— | n = 1-10000 |
| d) | —(X)$_n$— | n = 1-20 |
| e) | Z—(X)$_n$— | n = 0-20 |

-continued

| f) | —(X)$_n$—W | n = 0-20 |
| g) | Z—(X)$_n$—W | n = 0-20 | wherein

R denotes H, $(C_1\text{-}C_8)$-alkyl, $(C_6\text{-}C_{18})$-aryl, $(C_7\text{-}C_{19})$-aralkyl, $((C_1\text{-}C_8)\text{-alkyl})_{1\text{-}3}\text{-}(C_6\text{-}C_{18})$-aryl, X denotes $(C_6\text{-}C_{18})$-arylene, $(C_1\text{-}C_8)$-alkylene, $(C_1\text{-}C_8)$-alkenylene, $((C_1\text{-}C_8)\text{-alkyl})_{1\text{-}3}\text{-}(C_6\text{-}C_{18})$-arylene, $(C_7\text{-}C_{19})$-aralkylene,

Z, W denote, independently of one another, —C(=O)O—, —C(=O)NH—, —C(=O)—, NR, O, CHR, CH$_2$, C=S, S, PR.

Other preferred compounds that can be used as linkers are shown in the following diagram:

However, linkers such as e.g. 1,4'-biphenyl, 1,2-ethylene, 1,3-propylene, PEG-(2-10), α,ω-siloxanylene or 1,4-phenylene as well as α,ω-1,4-bisethylenebenzene or linkers obtainable from siloxanes of the general formula IV are especially preferred.

R: Me, Et
n = 0-10

These can easily be bound to any double bonds present in the polymers and suitable functional groups of the active centres under hydrosilylation conditions (overview of the hydrosilylation reaction by Ojima in The Chemistry of Organic Silicon Compounds, 1989 John Wiley & Sons Ltd., 1480-1526).

The size of the polymer enlargement should preferably be calculated such that the actual catalyst (formed from optionally polymer-enlarged ligand and transition metal) dissolves in the solvent to be used, so work can be performed in a homogeneous phase. The polymer-enlarged complex/catalyst used is preferably therefore a homogeneously soluble one. As a result, negative effects, which occur as a result of the phase change of the substrates and products otherwise necessary with the use of heterogeneous catalysts, can be avoided. The polymer-enlarged ligands can have an average molecular weight in the range of 1,000-1,000,000, preferably 5,000-500,000, particularly preferably 5,000-300,000, g/mol.

It lies within the framework of the invention that the above-mentioned components of the polymer-enlarged catalysts (I) to (IV) (polymer, linker, ligand) can be combined at will in accordance with the knowledge of a person skilled in the art to achieve an optimum reaction.

Combination of Polymer Enlargement with Linker/Ligand:

In principle there are two ways in which linkers/ligands can be attached to the polymer enlargement:
a) the active unit causing the chiral induction (ligand) is bound with an attached linker or directly to a monomer and this is copolymerised with other unmodified monomers, or
b) the active unit causing the chiral induction (ligand) is bound with a linker or directly to the finished polymer.

Polymers according to a) or b) can optionally be prepared and block-copolymerised with other polymers, which also exhibit the active units causing the chiral induction (ligand) or which do not exhibit them.

In principle, it is also true for the number of linkers/ligands per monomer in the polymer that as many as possible of these catalytically active units (ligands) should be accommodated in a polymer, so that the conversion per polymer enlargement is increased as a result. On the other hand, however, the ligands should be sufficiently spaced apart so that a reciprocal negative effect on the reactivity (TOF, selectivity) is minimised or completely avoided. Preferably, therefore, the distance between the linkers/ligands in the polymer should be in the range of 1-200 monomer units, preferably 5-25 monomer units.

In an advantageous embodiment, those positions in the polymer or monomer to be polymerised that can readily be functionalised, or allow an existing functionality to be used for the link, are used for attaching the linker/ligand. Thus, heteroatoms or unsaturated carbon atoms are preferably suitable for constructing the link.

In the case of styrene/polystyrene as polymer enlargement, for example, the existing aromatics can be used as connecting points to the linkers/ligands. Functionalities can be readily attached to these aromatics, preferably in 3-, 4- or 5-position, particularly preferably in 4-position, by means of standard aromatic chemistry. However, it is also advantageous to mix e.g. already functionalised monomer into the mixture to be polymerised and to bond the linker/ligand to the functionalities present in the polystyrene after the polymerisation. Advantageously suitable for this purpose are e.g. para-hydroxy-, para-chloromethyl- or para-aminostyrene derivatives.

In the case of polyacrylates, an acid group or ester group is present in the monomer component in each case, to which the linker or the active unit can be linked before or after the polymerisation, preferably via an ester or amide bond.

Polysiloxanes as polymer enlargement are preferably constructed in such a way that, in addition to dimethylsilane units, hydromethylsilane units are also present. The linkers/ligands can then also be attached to these positions by a hydrosilylation. These can preferably be linked to the functionalities under consideration in the polymer under hydrosilylation conditions (overview of the hydrosilylation reaction by Ojima in The Chemistry of Organic Silicon Compounds, 1989 John Wiley & Sons Ltd., 1480-1526).

Suitable polysiloxanes modified in this way are known in the literature ("Siloxane polymers and copolymers" White et al., in Ed. S. Patai "The Chemistry of Organic Silicon Compounds" Wiley, Chichester, 1989, 46, 2954; C. Wandrey et al. TH: Asymmetry 1997, 8, 1975).

Combination of Linker with Active Unit:

That which applies to the joining of polymer to linker/ligand, is synonymously applicable to the attaching of the ligand (active unit) to the linker.

Thus, the linker attachment to the active units can preferably take place via heteroatoms or certain functionalities such as C=O, $CH_2$, O, N, S, P, Si or B, ether-/thioether bonds, amine bonds or amide bonds preferably being linked, or esterifications, alkylations, silylations and additions to double bonds being carried out.

Those linking methods already described in the prior art for the polymer enlargement of the monomeric active units are particularly preferred (WO98/35927; Chem. Commun. 1999, 1917; Angew. Chem. 1997, 16, 1835; J. Am. Chem. Soc. 1996, 118, 7632; Tetrahedron Lett. 1997, 38, 1527; Eur. J. Org. Chem. 1998, 21; Angew. Chem. 1997, 109, 773; Chem. Commun. 1997, 2353; Tetrahedron: Asymmetry 1995, 6, 2687; ibid 1993, 4, 2351; Tetrahedron Lett. 1995, 36, 1549; Synlett 1999, 8, 1181; Tetrahedron: Asymmetry 1996, 7, 645; Tetrahedron Lett. 1992, 33, 5453; ibid 1994, 35, 6559; Tetrahedron 1994, 50, 11321; Chirality 1999, 11, 745; Tetrahedron Lett. 1991, 32, 5175; Tetrahedron Lett. 1990, 31, 3003; Chem. Commun. 1998, 2435; Tetrahedron Lett. 1997, 38, 2577).

The production of a polymer-enlarged ligand system or catalyst for the purpose of the invention can also be carried out, in principle, according to the specification in DE10029600.

Ligands of the general formula (III) or (IV)

(III)

(IV)

wherein

A and Q have the meaning given above, R'=H or R, and R, independently of one another in each case, denotes ($C_1$-$C_8$)-alkyl, HO—($C_1$-$C_8$)-alkyl, ($C_2$-$C_8$)-alkoxyalkyl, ($C_6$-$C_{18}$)-aryl, ($C_7$-$C_{19}$)-aralkyl, ($C_1$-$C_8$)-alkyl-($C_6$-$C_{18}$)-aryl, ($C_3$-$C_8$)-cycloalkyl, ($C_1$-$C_8$)-alkyl-($C_3$-$C_8$)-cycloalkyl or ($C_3$-$C_8$)-cycloalkyl-($C_1$-$C_8$)-alkyl, are also preferred. Ligands of the structures (III) and (IV) shown above, in which R is methyl, ethyl, propyl, iso-propyl, tert.-butyl or phenyl, are extremely preferred. Structures in which Q is oxygen or NR', wherein R' is ($C_1$-$C_8$)-alkyl, ($C_6$-$C_{18}$)-aryl or benzyl, and those in which Q is oxygen or NR', wherein R' is methyl, ethyl, propyl, iso-propyl, tert.-butyl, phenyl, naphthyl, fluorenyl or benzyl, are also extremely preferred.

The ligands according to the invention shown should, if possible, possess a high enantiomeric purity. The compounds of formulae (I) to (IV) should preferably possess an enantiomeric enrichment of >90%, more preferably >98%.

Another aspect of the invention provided relates to complexes containing the ligands according to the invention with at least one transition metal. Palladium, platinum, rhodium, ruthenium, osmium, iridium, cobalt, nickel or copper, in any catalytically relevant oxidation stage, are suitable as transition metals. These complex compounds are obtainable in solution by simply adding the ligands according to the invention to metal complex precursors, with which the person skilled in the art is familiar.

In another form, the invention also relates to a process for the production of the ligands according to the invention, wherein the corresponding phosphines are obtained by reacting LiP(SiMe$_3$)$_2$ with corresponding co-reactants provided with nucleofuge leaving groups in the presence of an organometallic base. Alkyl metals, such as e.g. n-, sec-, tert.-BuLi, MeLi, or the like, can be used as the organometallic base.

The trimethylsilylphosphines thus obtained are preferably reacted with the corresponding dihalogen derivative of the structures of group A illustrated above, the halogen atoms each being positioned on the free valencies of the structures shown.

One method of producing a group of the ligands according to the invention will be described below by way of an example. For the sake of clarity, maleic anhydride derivatives were selected in the illustrations, without thereby implying any restrictions or limitations for A.

In general, the procedure is to react an enantiomer-enriched sulfate with a phosphine in the presence of a strong base to form the monophospholane. In another reaction step, the phosphorus-carbon bond is split with the aid of an alkali metal and converted to silyl phospholane by adding a halogen silyl compound. In the following step, the silyl phospholane is reacted with 2,3-dichloromaleic anhydride or a 2,3-dichloromaleamide derivative to form the bisphospholane.

The diol is converted to the dimesylate in the presence of a nitrogen base and then converted to the phospholane in the presence of Li$_2$PPh$_2$-THF (*Tetrahedron Asymmetry* 1991, 2, 569-592).

The phospholane is also obtained by reacting the cyclic sulfate with H$_2$PPh in the presence of an alkali metal hydride (*J. Am. Chem. Soc.* 1999, 121, 9899-9900).

Another alternative preparation of the phospholane is achieved by reacting the cyclic sulfate with phenylphosphine in the presence of butyllithium.

After splitting the Ph-P bond with elementary lithium the P-silylated compound is obtained by adding trimethylsilyl chloride.

An alternative synthesis route involves the reaction of the cyclic sulfate with lithium bis(trimethylsilyl)phosphine (*Organometallics* 2000, 19, 250). Instead of the methanolysis of the phosphorus-silicon bonds described by Burk et al., it has proved advantageous in the synthesis of the ligands according to the invention to perform ring closure by adding methyllithium to form the trimethylsilyl-substituted phospholane.

In both reaction routes, the formation of the trimethylsilyl-substituted phospholane in meso-form is observed as a side reaction.

In the following step, the reaction of silyl phospholane with a 2,3-dichloromaleic acid derivative takes place analogously to a coupling reaction of Fenske et al. and Kinting et al. (*Chem. Ber.* 1974, 107, 117; *J. Organomet. Chem.* 1986, 302, 259).

The purification of the ligand takes place by the formation of the metal complex. Here, surprisingly, it has been found that a complex is obtained in optically pure form from the diastereomeric mixture of the ligand-metal compounds.

The compounds of the general formulae (I)-(IV) can be used as ligands for complex compounds in asymmetric, metal-catalysed reactions (such as e.g. hydrogenation, hydroformylation, rearrangement, allylic alkylation, cyclopropanation, hydrosilylation, hydride transfers, hydroborations, hydrocyanations, hydrocarboxylations, aldol reactions or Heck reaction). They are particularly suitable for asymmetric reactions.

Suitable complexes, particularly of the general formula (V), contain ligands according to the invention of formulae (I)-(IV) as ligands, $$[M_xP_yL_zS_q]A_r \qquad (V)$$

wherein, in general formula (V), M denotes a metal centre, preferably a transition metal centre, L denotes the same or different, coordinating, organic or inorganic ligands and P denotes bidentate organophosphorus ligands of formulae (I)-(IV) according to the invention, S represents coordinating solvent molecules and A represents equivalents of non-coordinating anions, wherein x and y are whole numbers greater than or equal to 1, and z, q and r are whole numbers greater than or equal to 0.

The sum of y+z+q has an upper limit set by the coordination centres available at the metal centres, it being unnecessary for all the coordination positions to be occupied. Complex compounds with an octahedral, pseudo-octahedral, tetrahedral, pseudo-tetrahedral or square-planar coordination sphere, which can also be distorted around the transition metal centre in each case, are preferred. The sum of y+z+q is less than or equal to 6 in these complex compounds.

The complex compounds according to the invention contain at least one metal atom or ion, preferably a transition metal atom or ion, particularly of palladium, platinum, rhodium, ruthenium, osmium, iridium, cobalt, nickel or copper in any catalytically relevant oxidation stage.

Complex compounds with fewer than four metal centres are preferred, and those with one or two metal centres are particularly preferred. The metal centres can be occupied by various metal atoms and/or ions.

Preferred ligands L of these complex compounds are halide, particularly Cl, Br and I, diene, particularly cyclooctadiene, norbornadiene, olefin, particularly ethylene and cyclooctene, acetato, trifluoroacetato, acetylacetonato, allyl, methallyl, alkyl, particularly methyl and ethyl, nitrile, particularly acetonitrile and benzonitrile, and also carbonyl and hydrido ligands.

Preferred coordinating solvents S are amines, particularly triethylamine, alcohols, particularly methanol and aromatics, particularly benzene and cumene.

Preferred non-coordinating anions A are trifluoroacetate, trifluoromethane sulfonate, $BF_4$, $ClO_4$, $PF_6$, $SbF_6$ and $BAr_4$.

Different molecules, atoms or ions of the individual components M, P, L, S and A can be contained in the individual complex compounds.

Among the ionically constructed complex compounds, compounds of the [RhP(diene)]$^+$A$^-$ type are preferred, wherein P represents a ligand of formulae (I)-(IV) according to the invention.

The preparation of these metal-ligand complex compounds can take place in situ by the reaction of a metal salt or a corresponding pre-complex with the ligands of the general formulae (I)-(IV). In addition, a metal-ligand complex compound can be obtained by reaction of a metal salt or a corresponding pre-complex with the ligands of the general formulae (I)-(IV) and subsequent isolation.

Examples of the metal salts are metal chlorides, bromides, iodides, cyanides, nitrates, acetates, acetylacetonates, hexafluoroacetylacetonates, tetrafluoroborates, perfluoroacetates or triflates, particularly of palladium, platinum, rhodium, ruthenium, osmium, iridium, cobalt, nickel or copper.

Examples of the Pre-Complexes are:
Cyclooctadienepalladium chloride, cyclooctadienepalladium iodide,
1,5-hexadienepalladium chloride, 1,5-hexadienepalladium iodide, bis(dibenzylideneacetone)palladium, bis(acetonitrile)palladium(II) chloride, bis(acetonitrile)palladium(II) bromide, bis(benzonitrile)palladium(II) chloride, bis(benzonitrile)palladium(II) bromide, bis(benzonitrile)palladium(II) iodide, bis(allyl)palladium, bis(methallyl)palladium, allylpalladium chloride dimer, methallylpalladium chloride dimer, tetramethylethylenediaminepalladium dichloride, tetramethylethylenediaminepalladium dibromide, tetramethylethylenediaminepalladium diiodide, tetramethylethylenediaminepalladium dimethyl,
cyclooctadieneplatinum chloride, cyclooctadieneplatinum iodide, 1,5-hexadieneplatinum chloride, 1,5-hexadieneplatinum iodide, bis(cyclooctadiene)platinum, potassium (ethylenetrichloroplatinate),
cyclooctadienerhodium(I) chloride dimer, norbornadienerhodium(I) chloride dimer,
1,5-hexadienerhodium(I) chloride dimer, tris(triphenylphosphane)rhodium(I) chloride,
hydridocarbonyltris(triphenylphosphane)rhodium(I) chloride,
bis(cyclooctadiene)rhodium(I) perchlorate, bis(cyclooctadiene)rhodium(I) tetrafluoroborate, bis(cyclooctadiene)rhodium(I) triflate, bis(acetonitrilecyclooctadiene)rhodium(I) perchlorate, bis(acetonitrilecyclooctadiene)rhodium(I) tetrafluoroborate, bis(acetonitrilecyclooctadiene)rhodium(I) triflate,
cyclopentadienerhodium(III) chloride dimer, pentamethylcyclopentadienerhodium(III) chloride dimer, (cyclooctadiene)Ru($\eta^3$-allyl)$_2$, ((cyclooctadiene)Ru)$_2$ (acetate)$_4$, ((cyclooctadiene)Ru)$_2$ (trifluoroacetate)$_4$, RuCl$_2$(arene) dimer, tris(triphenylphosphane)ruthenium(II) chloride, cyclooctadieneruthenium(II) chloride, OsCl$_2$(arene) dimer, cyclooctadieneiridium(I) chloride dimer, bis(cyclooctene)iridium(I) chloride dimer,
bis(cyclooctadiene)nickel, (cyclododecatriene)nickel, tris(norbornene)nickel, nickel tetracarbonyl, nickel(II) acetylacetonate,
(arene)copper triflate, (arene)copper perchlorate, (arene)copper trifluoroacetate, cobalt carbonyl.

The complex compounds based on one or more metals of the metallic elements, particularly from the group of Ru, Co, Rh, Ir, Ni, Pd, Pt and Cu, can already be catalysts or can be used to produce catalysts based on one or more metals of the metallic elements, particularly from the group of Ru, Co, Rh, Ir, Ni, Pd, Pt and Cu. All these complex compounds are particularly suitable in the asymmetric hydrogenation of C=C—, C=O— or C=N-bonds, in which they exhibit high activities and selectivities, and in asymmetric hydroformylation. In particular, it proves advantageous here that the ligands of the general formulae (I)-(IV) can be very well adapted, sterically and electronically, to the particular substrate and the catalytic reaction owing to their simple, broad adaptability.

Corresponding catalysts contain at least one of the complex compounds according to the invention.

As already indicated, the use of the complexes or catalysts according to the invention is particularly suitable for the hydrogenation of E/Z mixtures of prochiral N-acylated β-aminoacrylic acids or their derivatives. Acetyl, formyl or urethane or carbamoyl protective groups can preferably be used here as the acyl group.

In principle, the ligands and complexes/catalysts are used in a way known to the person skilled in the art in the form of transfer hydrogenation ("Asymmetric transfer hydrogenation of C=O and C=N bonds", M. Wills et al. Tetrahedron: Asymmetry 1999, 10, 2045; "Asymmetric transfer hydrogenation catalyzed by chiral ruthenium complexes" R. Noyori et al. Acc. Chem. Res. 1997, 30, 97; "Asymmetric catalysis in organic synthesis", R. Noyori, John Wiley & Sons, New York, 1994, p. 123; "Transition metals for organic Synthesis" Ed. M. Beller, C. Bolm, Wiley-VCH, Weinheim, 1998, vol. 2, p. 97; "Comprehensive Asymmetric Catalysis" Ed.: Jacobsen, E. N.; Pfaltz, A.; Yamamoto, H., Springer-Verlag, 1999), but it can also proceed conventionally with elemental hydrogen. The process can thus operate either by hydrogenation with hydrogen gas or by transfer hydrogenation.

In enantioselective hydrogenation, the preferred procedure is to dissolve the substrate to be hydrogenated and the complex/catalyst in a solvent. The catalyst is preferably formed from a pre-catalyst as indicated above, in the presence of the chiral ligand, by reaction or by pre-hydrogenation before the substrate is added. Hydrogenation is then performed at 0.1 to 10 bar, preferably 0.5 to 5 bar, hydrogen pressure.

The temperature during hydrogenation should be selected such that the reaction proceeds sufficiently rapidly with the desired enantiomeric excesses, but side reactions are avoided as far as possible. It is advantageous to work at temperatures of −20° C. to 100° C., preferably 0° C. to 50° C. The ratio of substrate to catalyst is determined by economic factors. The reaction should be carried out sufficiently rapidly with the lowest possible complex/catalyst concentration. However, it is preferable to work with a substrate/catalyst ratio of between 10000:1 and 10:1, preferably 1000:1 and 50:1.

Figure 1:
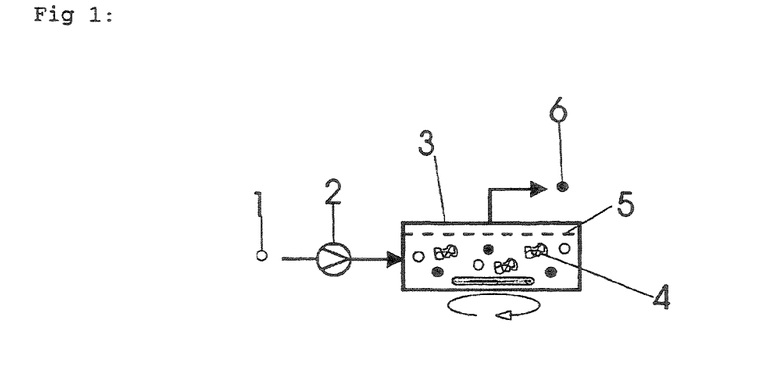
Figure 2:
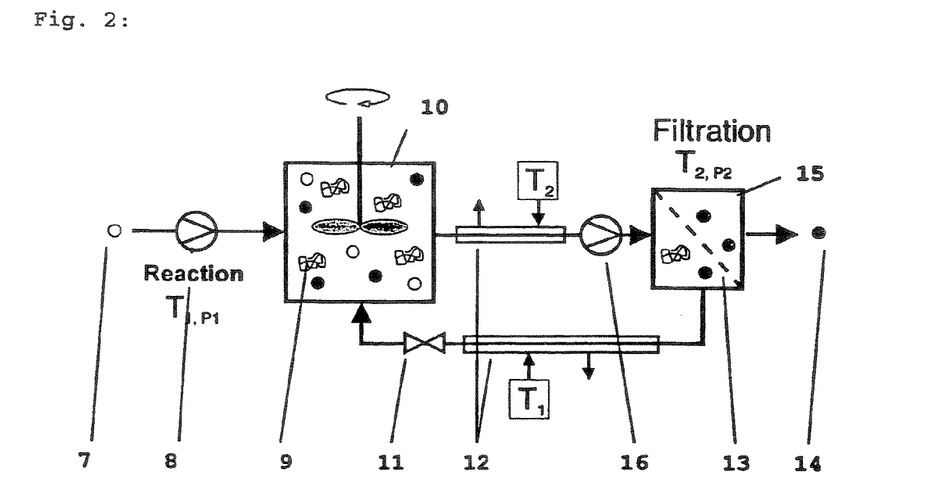

The use of the polymer-enlarged ligands or complexes is advantageous in catalytic processes carried out in a membrane reactor. The continuous operation that is possible in this apparatus, in addition to batch and semi-continuous operation, can be carried out in the cross-flow filtration mode (FIG. 2) or as dead-end filtration (FIG. 1), as desired.

Both process variants are described in principle in the prior art (Engineering Processes for Bioseparations, Ed.: L. R. Weatherley, Heinemann, 1994, 135-165; Wandrey et al., Tetrahedron Asymmetry 1999, 10, 923-928).

For a complex/catalyst to appear suitable for use in a membrane reactor, it has to fulfil many different criteria. On the one hand, for example, it should be ensured that there must be a sufficiently high retention capacity for the polymer-enlarged complex/catalyst so that there is satisfactory activity in the reactor over a desired period, without complex/catalyst having to be continually added, which is disadvantageous from the point of view of process economy (DE19910691). In addition, the catalyst used must have an appropriate tof (turn over frequency), to be able to convert the substrate into the product within economically reasonable periods.

In general the β-amino acid precursors were prepared in accordance with specifications from the literature. For the syntheses of the compounds, guidance can be taken from the general specifications by Zhang et al. (G. Zhu, Z. Chen, X. Zhang J. Org. Chem. 1999, 64, 6907-6910) and Noyori et al. (W. D. Lubell, M. Kitamura, R. Noyori Tetrahedron: Asymmetry. 1991, 2, 543-554) and also Melillo et al. (D. G. Melillo, R. D. Larsen, D. J. Mathre, W. F. Shukis, A. W. Wood, J. R. Colleluori J. Org. Chem. 1987 52, 5143-5150). Starting from the corresponding 3-ketocarboxylates, the desired prochiral enamides were obtained by reaction with ammonium acetate and subsequent acylation. The hydrogenation products can be converted to the β-amino acids by measures known to the person skilled in the art (analogous to the α-amino acids).

Within the framework of the invention, mixtures of polymer-enlarged polymers refer to the fact that individual polymers of different origins are polymerised together into block polymers. Random mixtures of the monomers in the polymer are also possible.

Polymer enlargement within the framework of the invention refers to the fact that one or more active units causing chiral induction (ligands) are copolymerised in a suitable form with other monomers or that these ligands are attached to an existing polymer by methods known to the person skilled in the art. Forms of the units suitable for copolymerisation are well known to the person skilled in the art and can be freely selected by him. The procedure is preferably such that the molecule in question is derivatised with groups capable of copolymerisation, according to the type of copolymerisation, e.g. in the case of copolymerisation with (meth)acrylates, by attaching to acrylate molecules.

Methyl, ethyl, n-propyl, isopropyl, n-butyl, isobutyl, sec-butyl, tert-butyl, pentyl, hexyl, heptyl or octyl, together with all their bond isomers, can be considered as $(C_1-C_8)$-alkyl radicals.

The $(C_1-C_8)$-alkoxy radical corresponds to the $(C_1-C_8)$-alkyl radical, with the proviso that this is bonded to the molecule via an oxygen atom.

As $(C_2-C_8)$-alkoxyalkyl, radicals in which the alkyl chain is interrupted by at least one oxygen function are meant, wherein two oxygen atoms cannot be joined to one another. The number of carbon atoms gives the total number of carbon atoms contained in the radical.

A $(C_3-C_5)$-alkylene bridge is a carbon chain with three to five C atoms, this chain being bonded to the molecule in question via two different C atoms.

The radicals just described can be mono- or polysubstituted with halogens and/or radicals containing N, O, P, S or Si atoms. These are particularly alkyl radicals of the type mentioned above having one or more of these heteroatoms in their chain or being bonded to the molecule via one of these heteroatoms.

$(C_3-C_8)$-Cycloalkyl means cyclopropyl, cyclobutyl, cyclopentyl, cyclohexyl or cycloheptyl radicals etc. These can be substituted with one or more halogens and/or radicals containing N, O, P, S or Si atoms and/or can have N, O, P or S atoms in the ring, such as e.g. 1-, 2-, 3-, 4-piperidyl, 1-, 2-, 3-pyrrolidinyl, 2-, 3-tetrahydrofuryl, 2-, 3-, 4-morpholinyl.

A $(C_3-C_8)$-cycloalkyl-$(C_1-C_8)$-alkyl radical refers to a cycloalkyl radical as set out above, which is bonded to the molecule via an alkyl radical as stated above.

$(C_1-C_8)$-Acyloxy within the framework of the invention means an alkyl radical as defined above with a maximum of 8 C atoms, which is bonded to the molecule via a COO— function.

$(C_1-C_8)$-Acyl within the framework of the invention means an alkyl radical as defined above with a maximum of 8 C atoms, which is bonded to the molecule via a CO— function.

A $(C_6-C_{18})$-aryl radical is understood to mean an aromatic radical with 6 to 18 C atoms. These include in particular compounds such as phenyl, naphthyl, anthryl, phenanthryl or biphenyl radicals, or systems of the type described above annelated to the molecule in question, such as e.g. indenyl systems, which can optionally be substituted with $(C_1-C_8)$-alkyl, $(C_1-C_8)$-alkoxy, $NR^1R^2$, $(C_1-C_8)$-acyl or $(C_1-C_8)$-acyloxy.

A $(C_7-C_{19})$-aralkyl radical is a $(C_6-C_{18})$-aryl radical bonded to the molecule via a $(C_3-C_8)$-alkyl radical.

A $(C_3-C_{18})$-heteroaryl radical within the framework of the invention refers to a five-, six- or seven-membered aromatic ring system of 3 to 18 C atoms, which contains heteroatoms such as e.g. nitrogen, oxygen or sulfur in the ring. In particular, radicals such as 1-, 2-, 3-furyl, such as 1-, 2-, 3-pyrrolyl, 1-, 2-, 3-thienyl, 2-, 3-, 4-pyridyl, 2-, 3-, 4-, 5-, 6-, 7-indolyl, 3-, 4-, 5-pyrazolyl, 2-, 4-, 5-imidazolyl, acridinyl, quinolinyl, phenanthridinyl and 2-, 4-, 5-, 6-pyrimidinyl are considered as such heteroaromatics.

A $(C_4-C_{19})$-heteroaralkyl means a heteroaromatic system corresponding to the $(C_7-C_{19})$-aralkyl radical.

Fluorine, chlorine, bromine and iodine are suitable as halogens (Hal).

PEG means polyethylene glycol.

The term enantiomer-enriched or enantiomeric excess within the framework of the invention means the proportion of an enantiomer in a mixture with its optical antipode in a range of >50% and <100%. The ee value is calculated as follows:

([Enantiomer1]−[Enantiomer2])/([Enantiomer1]+[Enantiomer2])=ee value

The naming of the complexes and ligands according to the invention contains, within the framework of the invention, all possible diastereomers, the two optical antipodes of any diastereomer also being included therein.

The complexes and catalysts described here determine, with their configuration, the optical induction in the product. It goes without saying that the catalysts, when used racemically, also yield racemic product. A subsequent resolution of racemates then yields the enantiomer-enriched products again. However, this is part of the general knowledge of the person skilled in the art.

N-Acyl groups mean protective groups that are conventionally used in amino acid chemistry for the protection of nitrogen atoms. The following can be particularly mentioned in this capacity: formyl, acetyl, Moc, Eoc, phthalyl, Boc, Alloc, Z, Fmoc, etc.

The literature references cited in this document are deemed to be contained in the disclosure.

Within the framework of the invention, membrane reactor means any reaction vessel in which the molecular weight-enlarged catalyst is enclosed in a reactor while low molecular weight substances are fed into the reactor or can leave it. The membrane can be integrated directly into the reaction chamber or can be installed outside it in a separate filtration module, in which the reaction solution flows continuously or intermittently through the filtration module and the retentate is recycled into the reactor. Suitable embodiments are described in WO98/22415 and in Wandrey et al. in Jahrbuch 1998, Verfahrenstechnik und Chemieingenieurwesen, VDI p. 151 ff.; Wandrey et al. in Applied Homogeneous Catalysis with organometallic Compounds, Vol. 2, VCH 1996, p. 832 ff.; Kragl et al., Angew. Chem. 1996, 6, 684 f., among others.

Within the framework of the invention, a polymer-enlarged ligand/complex means one in which the molecular weight-enlarging polymer is covalently bonded to the ligand.

DESCRIPTIONS OF THE DRAWINGS

FIG. 1 shows a membrane reactor with dead-end filtration. The substrate 1 is transferred via a pump 2 into the reactor chamber 3, which has a membrane 5. In the agitator-driven reactor chamber, in addition to the solvent, the catalyst 4, the product 6 and unreacted substrate 1 are found. Mainly low-molecular weight substances 6 are filtered off through the membrane 5.

FIG. 2 shows a membrane reactor with cross-flow filtration. Here, the substrate 7 is transferred via the pump 8 into the agitated reactor chamber, in which solvent, catalyst 9 and product 14 are also found. By means of the pump 16 a solvent flow is set up, which passes via an optionally present heat exchanger 12 into the cross-flow filtration cell 15. Here the low molecular-weight product 14 is separated off by means of the membrane 13. High molecular-weight catalyst 9 is then passed back into the reactor 10 with the solvent flow, optionally via a heat exchanger 12 again, optionally via the valve 11.

EXAMPLES

General

Reactions of air-sensitive compounds were performed in an argon-filled glove box or in standard Schlenk tubes. Solvents tetrahydrofuran (THF), diethyl ether and dichloromethane were degassed and purified by means of solvent-drying equipment (Innovative Technologies) by filtration through a column filled with activated aluminium oxide; toluene and pentane were additionally freed of oxygen by a column filled with a copper catalyst.

The following examples serve to explain the invention. They are not in any way intended to represent a limitation.

Example 1

(R,R)-2,5-Dimethyl-1-phenyl-phospholane

One equivalent of n-BuLi (8.9 ml, 1.6 M. solution in n-hexane) is added slowly to a solution of 1.57 g phenylphosphine (14.3 mmol) in 100 ml of THF at −78° C. This is then stirred for a further two hours at room temperature. After cooling again to −78° C., one equivalent of the cyclic sulfate 1 in 10 ml of THF is added via a cannula and the reaction is allowed to end by stirring at 25° C. for 3 hours. Before adding a further 1.2 eq. of n-BuLi (9.8 ml) via syringe, the mixture is cooled again, n-BuLi is added and stirring is continued overnight. For the work-up, the solvent was drawn off in vacuo and the residue taken up in 5 ml of water and extracted with 50 ml of methylene chloride. After the phase separation the solvent is removed and the residue is distilled in vacuo. An almost colourless syrup is obtained in a yield of 71% (1.95 g).

$Bp_{0.7}$=105° C.; $^1$H-NMR (CDCl$_3$): 7.51-7.45 (2H, m, arom. H); 7.35-7.30 (3H, m, arom. H), 2.70 (1H, m, CH—P), 2.31 (1H, m, H$_a$—CH$_2$), 2.22 (1H, m, CH—P), 1.97 (1H, m, H$_b$—CH$_2$), 1.47 (1H, m, H$_a$—CH$_2$), 1.34 (1H, m, H$_b$—CH$_2$), 1.33 (3H, dd, CH$_3$, $^3J_{H,P}$=19.0 Hz, $^3J_{H,H}$=7.1 Hz), 0.79 (3H, dd, CH$_3$, $^3J_{H,P}$=11.5 Hz, $^3J_{H,H}$=7.1 Hz); $^{13}$C-NMR (in CDCl$_3$): 137.7 (d, ipso-C, $^1J_{C,P}$=25.7 Hz), 134.1 (d, ortho-C, $^2J_{C,P}$=18.1 Hz), 128.4 (s, para-C), 127.8 (d, meta-C, $^3J_{C,P}$=6.6 Hz), 36.9 (d, CH$_2$, $^2J_{C,P}$=3.8 Hz), 36.8 (s, CH$_2$), 35.3 (d, CH—P, $^1J_{C,P}$=11.4 Hz), 34.8 (d, CH—P, $^1J_{C,P}$=8.6 Hz), 21.0 (d, CH$_3$, $^2J_{C,P}$=33.4 Hz), 15.1 (s, CH$_3$); $^{31}$P-NMR (in CDCl$_3$): 10.9; C$_{12}$H$_{17}$P (192.237).

Example 2

(R,R)-2,5-Dimethyl-1-trimethylsilyl-phospholane

According to the specification by Burk et al. (*Tetrahedron: Asymmetry* 1991, 2, 569-592), 3.06 g (15.9 mmol) of (R,R)-2,5-dimethyl-1-phenyl-phospholane in approx. 100 ml THF is taken at room temperature and 2.5 equivalents of lithium are added. The mixture is stirred overnight. The resulting deep-red suspension is separated from the lithium using a cannula and 2 equivalents of chlorotrimethylsilane (3.46 g) are slowly added at 0° C. using a syringe. Towards the end of the reaction, the reaction solution becomes almost colourless. The solution is concentrated in vacuo to 60-70% of its volume and the precipitated lithium salts are filtered off. After complete evaporation, the residue is distilled under reduced pressure and the silyl compound is obtained in a yield of 1.43 g (48%) as a colourless, liquid compound. The $^{31}$P-NMR spectrum discloses the presence of two species in a ratio of approx. 3:1. Based on an evaluation of the NMR signals, it is obviously the desired chiral silyl phospholane and the corresponding meso-compound. Isomerisation reactions of this type have already been described by Burk (*Tetrahedron: Asymmetry* 1991, 2, 569-592). Since, in the subsequent reaction with dichloromaleic anhydride, only one diastereomer crystallises out, this mixture of isomers could be used for the nucleophilic reaction without prior separation.

$Bp_{15}$=72-80° C.; $^1$H-NMR (CDCl$_3$): 2.54-1.20 (6H, m, CH—P, CH$_2$), 1.25-1.15 (6H, m, CH$_3$), 0.20 (d, Si(CH$_3$)$_3$, $^3J_{H,P}$=4.2 Hz), 0.15 (d, meso-Si(CH$_3$)$_3$, $^3J_{H,P}$=4.2 Hz), $^{13}$C-NMR (in CDCl$_3$): 40.1 (d, CH$_2$, $^2J_{C,P}$=4.8 Hz), 38.9 (s, CH$_2$), 37.5 (s, meso-CH$_2$), 33.6 (d, CH—P, $^1J_{C,P}$=11.4 Hz), 31.3 (d, CH—P, $^1J_{C,P}$=7.6 Hz), 30.5 (d, meso-CH—P, $^1J_{C,P}$=7.6 Hz), 23.4 (d, meso-CH$_3$, $^2J_{C,P}$=30.5 Hz), 22.8 (d, CH$_3$, $^2J_{C,P}$=30.5 Hz), 18.0 (d, CH$_3$, $^2J_{C,P}$=1.9 Hz), −0.2 (d, Si(CH$_3$)$_3$, $2J_{C,P}$=11.4 Hz), −1.8 (d, meso-Si(CH$_3$)$_3$, $^2J_{C,P}$=10.5 Hz); $^{31}$P-NMR (in CDCl$_3$): −53.1 (meso), −54.5; C$_9$H$_{21}$PSi (188, 322);

Example 3

(R,R)-2,5-Dimethyl-1-trimethylsilyl-phospholane

To a solution of 9.50 g of tris(trimethylsilyl)phosphine (37.9 mmol) in 300 ml of THF are added 0.1.05 eq. of MeLi (28.4 ml, 1.4 M solution in ether), slowly, at room temperature. Stirring is then continued overnight at room temperature and the solvent is then removed under vacuum. The residue is now taken up with 300 ml of ether and one equivalent of the cyclic sulfate is added (6.83 g in 100 ml of ether) dropwise to the lithium salt solution. After three hours, 28.4 ml of MeLi solution are again added to the reaction mixture using a syringe. To complete the reaction, the mixture is stirred overnight. For the workup, the solvent is removed in vacuo and the residue is carefully distilled in vacuo. A colourless, mobile syrup is obtained in a yield of 70% (5.0 g).

$Bp_{20}$=93° C.; $^1$H-NMR (CDCl$_3$): 2.54-1.20 (6H, m, CH—P, CH$_2$), 1.25-1.15 (6H, m, CH$_3$), 0.20 (9H, d, Si (CH$_3$)$_3$, $^3J_{H,P}$=4.2 Hz), $^{13}$C-NMR (in CDCl$_3$): 40.1 (d, CH$_2$, $^2J_{C,P}$=4.8 Hz), 38.9 (s, CH$_2$), 33.6 (d, CH—P, $^1J_{C,P}$=11.4 Hz), 31.3 (d, CH—P, $J_{C,P}$=7.6 Hz), 22.8 (d, CH$_3$, $^2J_{C,P}$=30.5 Hz), 18.0 (d, CH$_3$, $2J_{C,P}$=1.9 Hz), −0.2 (d, Si(CH$_3$)$_3$, $^2J_{C,P}$=11.4 Hz), $^{31}$P-NMR (in CDCl$_3$): −54.5; C$_9$H$_{21}$PSi (188, 322);

Example 4

2,3-Bis[(R,R)-2,5-dimethyl-phospholanyl]maleic anhydride

According to the specification by Fenske et al. (*Chem. Ber.* 1974, 107, 117-122) 450 mg (2.4 mmol) of the diastereomeric mixture of the silyl compound 3 were added dropwise using a syringe over a period of 15 minutes to a solution of 200 mg of 2,3-dichloromaleic anhydride (0.5 eq.) in 5 ml of diethyl ether at 0° C. The mixture was then kept at −78° C. overnight. The dark reddish-brown crystals that precipitated were isolated from the solvent by bag filtration and then dried. Yield 190 mg (49%).

In the NMR of the isolated compound, only one diastereomer of a C$_2$-symmetrical compound is found. This is the proof that the corresponding meso-silylphosphine, which was added to the reaction in a deficiency, either has not reacted or the corresponding diastereomeric products do not crystallise out. With this observation, a partial racemisation in the synthesis of the (R,R)-2,5-dimethyl-1-trimethylsilyl-phospholane can also be simultaneously ruled out. Its use should lead to diastereomeric bisphospholanes after phosphinylation, and these were not detected.

$^1$H-NMR (CDCl$_3$): 3.32 (2H, m, CH$_2$), 2.49-1.25 (10H, m, CH—P, CH$_2$), 1.22 (6H, dd, CH$_3$, $^3J_{H,P}$=20.4 Hz, $^3J_{H,H}$=7.3 Hz), 1.07 (6H, dd, CH$_3$, $^3J_{H,P}$=10.5 Hz, $^3J_{H,H}$=7.2 Hz); $^{13}$C-NMR (in CDCl$_3$): 163.7 (s, C=O), 37.7 (s, CH$_2$), 36.9 (s, CH$_2$), 36.6 (m, CH—P), 31.5 (s, CH—P), 20.5 (m, CH$_3$), 16.9 (s, CH$_3$); $^{31}$P-NMR (in CDCl$_3$): −2.2; C$_{16}$H$_{24}$O$_3$P$_2$ (326, 307);

Example 5

Rhodium Complexes by Reaction of the Ligand with [Rh(COD)$_2$]BF$_4$ 190 mg (0.58 mmol) of the bisphospholane are dissolved in 2 ml of THF and slowly added at approx. −20° C. to a solution of one equivalent of [Rh(COD)$_2$]BF$_4$ (236 mg). This is left to warm up to room temperature and stirred for a further 90 min. A brown precipitate slowly forms, which is washed twice with ether after being filtered off.

$^1$H-NMR (acetone-d$_6$): 5.85 (2H, s(br), =CH), 5.15 (2H, s(br), =CH), 3.07 (2H, m, CH—P), 2.67-1.50 (18H, m, CH—P, CH$_2$)$_1$ 1.57 (6H, dd, CH$_3$, $^3$J$_{H,P}$=19.5 Hz, $^3$J$_{H,H}$=7.0 Hz), 1.23 (6H, dd, CH$_3$, $^3$J$_{H,P}$=16.0 Hz, $^3$J$_{H,H}$=7.1 Hz); $^{13}$C-NMR (in acetone-d$_6$): 165.1 (m, C=C), 160.1 (m, C=O), 108.5 (=CH), 94.9 (=CH), 40.8 (m, CH—P), 38.0 (m, CH—P), 37.7 (s, CH$_2$), 36.4 (s, CH$_2$), 32.8 (s, CH$_2$), 29.0 (s, CH$_2$), 17.6 (m, CH$_3$), 14.1 (s, CH$_3$); $^{31}$P-NMR (in CDCl$_3$): 63.8 (d, $^1$J$_{P,Rh}$=151 Hz, [Rh(P—P) (COD)]BF$_4$);

Example 6

Hydrogenations

Conditions: Catalyst:substrate: 200:1; 1 mmol substrate, 15 ml methanol or THF, 25° C., 1.5 bar hydrogen.

| | THF | | Methanol | |
|---|---|---|---|---|
| Substrate | t (sample) | % ee/ conversion | t (sample) | % ee/ conversion |
| Methyl acetamido- cinnamate | 2 h | 95.5 (R) 100% | 0.5 h | 84.0 (R) 25% |
| | 6 h | 95.5 (R) 100% | 1 h | 87.4 (R) 50% |
| | 24 h | 95.5 (R) 100% | 2 h | 88.9 (R) 90% |
| Dimethyl itaconate | 0.5 h | 80.4 (S) 20% | 1 h | 2.9 (S) 20% |
| | 1 h | 79.1 (S) 50% | 2 h | 4.1 (S) 55% |
| | 2 h | 73.3 (S) 100% | 4 h | 3.1 (S) 100% |

Example 7

Hydrogenations of β-Amino Acid Precursors

Conditions: 0.005 mmol catalyst, 0.5 mmol substrate, 7.5 ml solvent, 1 bar hydrogen, 25° C.

| Substrate | Solvent | Catalyst (Example 4) | [Rh((S,S)-Me-DuPHOS) (COD)]BF$_4$ |
|---|---|---|---|
| Ph, AcNH, CO$_2$Et | MeOH | 85% ee (S) | 78% ee (R) |
| | THF | 82% ee (S) | 73% ee (R) |
| (iPr substituted, AcNH, CO$_2$Et) | MeOH | 69% ee (S) | 4% ee (R) |
| | THF | 63% ee (S) | 36% ee (R) |
| (iPr, CO$_2$Et, AcNH) | MeOH | 97% ee (S) | 99% ee (R) |
| | THF | 99% ee (S) | 98% ee (R) |
| Et, AcNH, CO$_2$Et | MeOH | 81% ee (S) | 68% ee (R) |

The invention claimed is:

1. A ligand represented by formula (1)

(1)

wherein
R is selected from the group consisting of (C$_1$-C$_8$)-alkyl, HO—(C$_1$-C$_8$)-alkyl, (C$_2$-C$_8$)-alkoxyalkyl, (C$_6$-C$_{18}$)-aryl, (C$_7$-C$_{19}$)-aralkyl, (C$_1$-C$_8$)-alkyl-(C$_6$-C$_{18}$)-aryl, (C$_3$-C$_8$)-cycloalkyl, (C$_1$-C$_8$)-alkyl-(C$_3$-C$_8$)-cycloalkyl and (C$_3$-C$_8$)-cycloalkyl-(C$_1$-C$_8$)-alkyl, Q is selected from the group consisting of O and N—R' and R' is selected from the group consisting of H, (C$_1$-C$_8$)-alkyl, (C$_6$-C$_8$)-aryl and (C$_1$-C$_8$)-alkyl-(C$_6$-C$_{18}$)-aryl.

2. The ligand according to claim 1, wherein R is selected from the group consisting of methyl, ethyl, propyl, iso-propyl, tert-butyl and phenyl.

3. The ligand according to claim 1, wherein the ligand has an enantiomer enrichment of greater than 90%.

4. A ligand of formula (2)

(2)

5. A ligand of formula (3)

(3)

6. A ligand of formula (4)

(4)

7. A complex comprising the ligand of claim 1 and at least one transition metal.

8. A complex comprising the ligand of claim 1 and at least one metal selected from the group consisting of palladium, platinum, rhodium, ruthenium, osmium, iridium, cobalt, nickel and copper.

9. A complex comprising the ligand of claim 1 and rhodium.

10. A complex comprising the ligand of claim 4 and at least one transition metal.

11. A complex comprising the ligand of claim 4 and at least one metal selected from the group consisting of palladium, platinum, rhodium, ruthenium, osmium, iridium, cobalt, nickel and copper.

12. A complex comprising the ligand of claim 4 and rhodium.

13. A complex comprising the ligand of claim 5 and at least one transition metal.

14. A complex comprising the ligand of claim 5 and at least one metal selected from the group consisting of palladium, platinum, rhodium, ruthenium, osmium, iridium, cobalt, nickel and copper.

15. A complex comprising the ligand of claim 5 and rhodium.

16. A complex of formula (5)

$$[M_xP_yL_zS_q]A_r \quad (5)$$

wherein
M denotes a metal,
L denotes a an organic or inorganic ligand,
P is the ligand of claim 1,
S is a coordinating solvent molecule, and
A is an anion;
wherein x and y are whole numbers greater than or equal to 1 and
wherein z, q, and r are whole numbers greater than or equal to 0.

17. The complex of claim 16, wherein the metal M is at least one transition metal.

18. The complex of claim 16, wherein the metal M is at least one metal selected from the group consisting of palladium, platinum, rhodium, ruthenium, osmium, iridium, cobalt, nickel and copper.

19. The complex of claim 16, wherein the ligand L is at least one ligand selected from the group consisting cyclooctadiene, norbornadiene, ethylene, cyclooctene, acetate, trifluoroacetato, acetylacetonato, allyl, methallyl, methyl, ethyl, acetonitrile, benzonitrile, carbonyl, and hydrido.

20. The complex of claim 16, wherein the anion A is at least one anion selected from the group consisting of trifluoromethane sulfonate, $BF_4^-$, $ClO_4^-$, $PF_6^-$, and $SbF_6^-$.

21. The complex of claim 16, wherein the solvent molecule S is at least one selected from the group consisting of triethylamine, methanol, benzene and cumeme.

22. The complex of claim 16, wherein
the metal M is at least one transition metal;
the ligand L is at least one ligand selected from the group consisting cyclooctadiene, norbornadiene, ethylene, cyclooctene, acetate, trifluoroacetato, acetyl acetonato, allyl, methallyl, methyl, ethyl, acetonitrile, benzonitrile, carbonyl, and hydrido;
the anion A is at least one anion selected from the group consisting of trifluoromethane sulfonate, $BF_4^-$, $ClO_4^-$, $PF_6^-$, and $SbF_6^-$; and
the solvent molecule S is at least one selected from the group consisting of triethylamine, methanol, benzene and cumene.

23. The complex of claim 16, wherein
the metal M is at least one metal selected from the group consisting of palladium, platinum, rhodium, ruthenium, osmium, iridium, cobalt, nickel and copper;
the ligand L is at least one ligand selected from the group consisting cyclooctadiene, norbornadiene, ethylene, cyclooctene, acetate, tri fluoroacetato, acetyl acetonato, allyl, methallyl, methyl, ethyl, acetonitrile, benzonitrile, carbonyl, and hydrido;
the anion A is at least one anion selected from the group consisting of trifluoromethane sulfonate, $BF_4^-$, $ClO_4^-$, $PF_6^-$, and $SbF_6^-$; and
the solvent S is at least one selected from the group consisting of triethylamine, methanol, benzene and cumene.

24. A complex of formula (6)

(6)

25. A complex of formula (7)

wherein R' is selected from the group consisting of H, $(C_1\text{-}C_8)$-alkyl, $(C_6\text{-}C_8)$-aryl and $(C_1\text{-}C_8)$-alkyl-$(C_6\text{-}C_{18})$-aryl.

26. A complex of formula (8)

27. A complex of formula (9)

28. A ligand represented by formula (10)

wherein

R is selected from the group consisting of $(C_1\text{-}C_8)$-alkyl, HO—$(C_1\text{-}C_8)$-alkyl, $(C_2\text{-}C_8)$-alkoxyalkyl, $(C_6\text{-}C_{18})$-aryl, $(C_7\text{-}C_{19})$-aralkyl, $(C_1\text{-}C_8)$-alkyl-$(C_6\text{-}C_{18})$-aryl, $(C_3\text{-}C_8)$-cycloalkyl, $(C_1\text{-}C_8)$-alkyl-$(C_3\text{-}C_8)$-cycloalkyl and $(C_3\text{-}C_8)$-cycloalkyl-$(C_1\text{-}C_8)$-alkyl,

Q is selected from the group consisting of O and N—R', and

R' is selected from the group consisting of H, $(C_1\text{-}C_8)$-alkyl, $(C_6\text{-}C_8)$-aryl, and $(C_6\text{-}C_{18})$-alkyl-$(C_6\text{-}C_{18})$-aryl.

29. The ligand according to claim 28, wherein R is selected from the group consisting of methyl, ethyl, propyl, iso-propyl, tert-butyl and phenyl.

30. The ligand according to claim 28, wherein the ligand has an enantiomer enrichment of greater than 90%.

31. A ligand of formula (11)

32. A ligand of formula (12)

33. A complex comprising the ligand of claim 28 and at least one transition metal.

34. A complex comprising the ligand of claim 28 and at least one metal selected from the group consisting of palladium, platinum, rhodium, ruthenium, osmium, iridium, cobalt, nickel and copper.

35. A complex comprising the ligand of claim 28 and rhodium.

36. A complex comprising the ligand of claim 31 and at least one transition metal.

37. A complex comprising the ligand of claim 31 and at least one metal selected from the group consisting of palladium, platinum, rhodium, ruthenium, osmium, iridium, cobalt, nickel and copper.

38. A complex comprising the ligand of claim 31 and rhodium.

39. A complex comprising the ligand of claim 32 and at least one transition metal.

40. A complex comprising the ligand of claim 32 and at least one metal selected from the group consisting of palladium, platinum, rhodium, ruthenium, osmium, iridium, cobalt, nickel and copper.

41. A complex comprising the ligand of claim 32 and rhodium.

42. A complex of formula (5)

$$[M_xP_yL_zS_q]A_r \quad (5)$$

wherein

M denotes a metal,

L denotes a an organic or inorganic ligand,

P is the ligand of claim 28,

S is a coordinating solvent molecule, and

A is an anion;

wherein x and y are whole numbers greater than or equal to 1 and wherein z, q, and r are whole numbers greater than or equal to 0.

43. The complex of claim 42, wherein the metal M is at least one transition metal.

44. The complex of claim 42, wherein the metal M is at least one metal selected from the group consisting of palladium, platinum, rhodium, ruthenium, osmium, iridium, cobalt, nickel and copper.

45. The complex of claim 42, wherein the ligand L is at least one ligand selected from the group consisting cyclooctadiene, norbornadiene, ethylene, cyclooctene, acetate, trifluoroacetato, acetylacetonato, allyl, methallyl, methyl, ethyl, acetonitrile, benzonitrile, carbonyl, and hydrido.

46. The complex of claim 42, wherein the anion A is at least one anion selected from the group consisting of trifluoromethane sulfonate, $BF_4^-$, $ClO_4^-$, $PF_6^-$, and $SbF_6^-$.

47. The complex of claim 42, wherein the solvent molecule S is at least one selected from the group consisting of triethylamine, methanol, benzene and cumeme.

48. The complex of claim 42, wherein the metal M is at least one transition metal;

the ligand L is at least one ligand selected from the group consisting cyclooctadiene, norbornadiene, ethylene, cyclooctene, acetate, trifluoroacetato, acetylacetonato, allyl, methallyl, methyl, ethyl, acetonitrile, benzonitrile, carbonyl, and hydrido;

the anion A is at least one anion selected from the group consisting of trifluoromethane sulfonate, $BF_4^-$, $ClO_4^-$, $PF_6^-$, and $SbF_6^-$; and the solvent molecule S is at least one selected from the group consisting of triethylamine, methanol, benzene and cumene.

49. The complex of claim 42, wherein the metal M is at least one metal selected from the group consisting of palladium, platinum, rhodium, ruthenium, osmium, iridium, cobalt, nickel and copper;

the ligand L is at least one ligand selected from the group consisting cyclooctadiene, norbornadiene, ethylene, cyclooctene, acetate, trifluoroacetato, acetylacetonato, allyl, methallyl, methyl, ethyl, acetonitrile, benzonitrile, carbonyl, and hydrido;

the anion A is at least one anion selected from the group consisting of trifluoromethane sulfonate, $BF_4^-$, $ClO_4^-$, $PF_6^-$, and $SbF_6^-$; and the solvent S is at least one selected from the group consisting of triethylamine, methanol, benzene and cumene.

50. A complex of formula (13)

51. A complex of formula (14)

52. The ligand according to claim 4, wherein the ligand has an enantiomer enrichment of greater than 90%.

53. The ligand according to claim 5, wherein the ligand has an enantiomer enrichment of greater than 90%.

54. The complex according to claim 24, wherein the complex has an enantiomer enrichment of greater than 90%.

55. The complex according to claim 25, wherein the complex has an enantiomer enrichment of greater than 90%.

56. The ligand according to claim 28, wherein the ligand has an enantiomer enrichment of greater than 90%.

57. The ligand according to claim 31, wherein the ligand has an enantiomer enrichment of greater than 90%.

58. The ligand according to claim 32, wherein the ligand has an enantiomer enrichment of greater than 90%.

59. The complex according to claim 50, wherein the complex has an enantiomer enrichment of greater than 90%.

60. The complex according to claim 51, wherein the complex has an enantiomer enrichment of greater than 90%.

61. The ligand of claim 1, wherein R' is H.

62. The ligand of claim 1, wherein R' is Me.

63. The complex of claim 26, wherein the complex has an enantiomer enrichment of >90%.

64. The complex of claim 27, wherein the complex has an enantiomer enrichment of >90%.

65. A ligand of formula (15)

66. A complex of formula (16)

\* \* \* \* \*